United States Patent [19]
Pryor

[11] Patent Number: 5,566,627
[45] Date of Patent: Oct. 22, 1996

[54] METHOD AND APPARATUS FOR OZONE TREATMENT OF SOIL TO KILL LIVING ORGANISMS

[76] Inventor: Alan E. Pryor, 655 S. Fair Oaks Ave., Apt. I-304, Sunnyvale, Calif. 94086

[21] Appl. No.: 332,628

[22] Filed: Oct. 31, 1994

Related U.S. Application Data

[63] Continuation-in-part of Ser. No. 184,333, Jan. 18, 1994.
[51] Int. Cl.$^6$ ................................. A01C 23/00
[52] U.S. Cl. ........................ 111/118; 111/120; 405/128; 405/258; 47/48.5; 47/58
[58] Field of Search ............................ 47/6, 9, 48.5, 58; 111/118, 120, 200, 7.2; 405/51, 128, 130, 131, 270, 258; 239/201, 207; 422/28, 32, 292

[56] References Cited

U.S. PATENT DOCUMENTS

| | | | |
|---|---|---|---|
| 3,413,940 | 12/1968 | Vissers | 111/120 |
| 4,293,237 | 10/1981 | Robey et al. | |
| 4,549,477 | 10/1985 | McCabe, Jr. | |
| 4,570,553 | 2/1986 | Ito | 111/118 |
| 4,632,044 | 12/1986 | Allen | 111/120 |
| 4,819,374 | 4/1986 | Gemgnami | 47/58 |
| 4,978,508 | 12/1990 | Hansen et al. | |
| 5,011,599 | 4/1991 | Kearney et al. | |
| 5,011,699 | 4/1991 | Mitsuda et al. | |
| 5,040,729 | 8/1991 | Carrozza | |
| 5,053,140 | 10/1991 | Hurst | |
| 5,221,312 | 6/1993 | Buhidar | 71/12 |
| 5,246,309 | 9/1993 | Hobby | |
| 5,259,962 | 11/1993 | Later | |
| 5,269,943 | 12/1993 | Wickramanayake | |
| 5,277,655 | 1/1994 | Storkan et al. | |

OTHER PUBLICATIONS

Block, Seymour S., "Disinfection, Sterilization, and Preservation", 3rd edition, published 1983 by Lea and Febiger, p. 673.

A 16–page document entitled "Ozone" reprinted from *Kirk:Othmer Encyclopedia of Chemical Technology*, vol. 16, Third Edition, pp. 684–713, 1961.

Alan Pryor, "Ozone Toxicology, Exposure Threshold Limit Values, and Safety Precautions," *Ozone News, International Ozone Association*, vol. 18, No. 6, pp. 1–8, Nov./Dec. 1990.

Synthesis Report of the Methyl Bromide Interim Scientific Assessment and Methyl Bromide Interim Technology and Economic Assessment requested by: United Nations Environment Programme, pp. 1–3 and 26, 27, and 31, Jun., 1992.

Patrick Cavanaugh, "Methyl Bromide Users Endure Changes," *Nut Grower*, pp. 12–14, Sep., 1993.

Patrick Cavanaugh, "Methyl Bromide Use Questioned," *Vegetable*, pp. 6–7, Sep./Oct., 1992.

An article on one page from *Vegetable*, Summer, 1993, entitled "Methyl Bromide Alternative Probed".

(List continued on next page.)

*Primary Examiner*—Terry Lee Melius
*Assistant Examiner*—Robert Pezzuto
*Attorney, Agent, or Firm*—Skjerven, Morrill, Macpherson, Franklin & Friel; Alan H. Macpherson; Omkar K. Suryadevara

[57] ABSTRACT

An ozone containing gas is injected into soil, preferably relatively dry and approximately uniform in consistency, to kill biological life forms. A soil injector injects ozone containing gas from an ozone supplier. In one embodiment, the ozone supplier is moved over the field by a structure such as a trailer or a vehicle. In another embodiment, a lattice arrangement of conduits is used to inject the ozone containing gas into the soil. The soil is optionally covered with a gas semipermeable or impermeable membrane subsequent to or prior to injection of the ozone containing gas. In yet another embodiment, the soil is transferred to a chamber and subjected to in-vitro ozone treatment. In accordance with this invention, the soil is exposed to a sufficient concentration of ozone for a sufficient period of time such that the ozone oxidizes the impurities thereby reducing detrimental organisms, and thus sanitizing the soil.

14 Claims, 9 Drawing Sheets

OTHER PUBLICATIONS

Larry Waterfield, "No Quick Fix for Methyl Bromide," *The Grower,* Nov., 1992.

F. Pauwels, "Soil Disinvestation in the Belgian Horticulture: A Practice View," 2 pages, 1989.

"Innovative in Situ Cleanup Processes"; *The Hazaradous Waste Consultant;* pp. 4.1, and 4.24–4.26; Sep./Oct. 1992.

Victor H. Dropkin, "Introduction to Plant Nematology", A Wiley–Interscience Publication, pp. 270–271 and 266, believed to be 1986.

Victor H. Dropkin, "Introduction to Plant Nematology", Second Edition, p. 278, A Wiley–Interscience Publication 1989.

"The Weakening Effect as a Trigger for Biological Control and Criteria for its Evaluation", Biological Control of Plant Diseases, Edited by E. S. Tjamos et al., Plenum Press, pp. 55–61 New York, 1992.

Heinz Decker, "Plant Nematodes and Their Control, Published for the United states Department of Agriculture and the National Science Foundation," Washington, D.C., by Amerind Publishing Co. Pvt.Ltd., p. 128, New Delhi 1981.

Christopher Z. Womersley, "Entomopathogenic Nematodes in Biological Control", *Dehydration Survival and Anhydrobiotic Potential,* p. 117, publication date unknown.

E. Mignard & J. C. Benet, "Diffusion of Methyl Bromide in Soil", Journal of Soil Science, pp. 151–153, 40, Publication 1989.

H. W. Lembright, *Soil Fumigation: Principles and Application Technology,* pp. 632–637, Supplement to Journal of Nematology, Vol. 22, pp. 632–637, Oct. 1990.

R. Vargas and T. Hattori, "The Distribution of Protozoa Within Soil Aggregates", Abstract, Journal of General and Applied Microbiology, 37: 6, pp. 515–518, 1991.

METHOD AND APPARATUS FOR OZONE TREATMENT OF SOIL TO KILL LIVING ORGANISMS

This application is a continuation-in-part of application U.S. Ser. No. 08/184,333, filed Jan. 18, 1994.

FIELD OF THE INVENTION

This invention relates to a method and apparatus for treatment of agricultural top soil to kill living organisms and, in particular, to a method and apparatus for exposing top soil suitable for plant growth purposes to an ozone containing gas to kill undesirable living organisms in the soil including, but not limited to, micro organisms, multicellular animals, plants and seeds.

BACKGROUND OF THE INVENTION

In the agricultural industry, there is a need to kill weeds, insects, nematodes, bacteria and other single celled or multi-celled living organisms in the top soil of a field, for example immediately prior to growing crops. One common and effective agriculturally used disinfecting agent for treatment of top soil is methyl bromide. Methyl bromide effectively destroys living cells once methyl bromide is transported across the cell wall of a living organism. After the methyl bromide treatment, the top soil is conventionally used for growing plants such as crops.

However, methyl bromide is being phased out of agricultural use due to its deleterious effect on the ozone layer and due to its human health hazards. Thus a substitute for methyl bromide is urgently needed for killing undesirable living organisms commonly found in agricultural top soil suitable for plant growth purposes.

Ozone in aqueous solutions, hereinafter "aqueous ozone," has been used for inhibition or reduction of biological life forms such as molds, fungi, bacteria, algae, in numerous applications including swimming pools, potable water, bottled water, aquaria, fish hatcheries, and cooling towers. Ozone in the gas phase, hereinafter "gaseous ozone," has been used primarily in the food processing industries for sanitization of the surfaces of, for example, fish, grains, delicate vegetables, and processed foods. Gaseous ozone has also been used as a sanitizing agent for disinfecting the surfaces of operating rooms, animal containment facilities, and air conditioning and heating ventilation systems and for deodorization in municipal waste treatment plants.

Application of aqueous ozone to soil is not expected to be effective to kill living organisms because aqueous ozone has the drawback of slow dispersion of water into and through the soil of a field. Also, aqueous ozone suffers from rapid breakdown of ozone, so that maintaining sufficiently high concentrations of ozone in the water in the soil can be difficult. Aqueous ozone has a half life on the order of minutes in ambient conditions.

Although gaseous ozone has a half life on the order of hours (up to 20 hours depending on ambient conditions), according to traditional thinking, if gaseous ozone were used for soil treatment, ozone would quickly dissolve in the entrapped soil moisture and rapidly break down.

To increase stability of gaseous ozone in the soil environment, U.S. Pat. No. 5,269,943 to Wickramanayake suggests that "ozone containing gas is treated with acid" (abstract) and that "[a]fter the decontamination process, if the soil is found to be too acidic, the pH may be increased to the required level by applying unacidified gas ozone mixture for some time." (Col. 9, lines 65–68).

In treatment of surfaces of foods with aqueous ozone, virtually all of the surface dwelling living organisms are exposed to ozone. Furthermore, even for treatment of food surfaces using gaseous ozone, all the living organisms on food surfaces are exposed to predetermined, fixed concentrations of ozone. Conventional thinking suggests that gaseous ozone dispersion would be inhibited by the compacted, compressed nature of soil in a field or that untoward emissions of ozone gas would escape from the soil in a field into the atmosphere and so minimize ozone's effectiveness.

Traditional thinking also indicated difficultly in maintaining sufficiently high concentrations of gaseous ozone in soil for the periods of time necessary to kill the living organisms that may be harbored and/or partially protected in either pores of individual soil particles or in the interstitial spaces in clumps of soil. Moreover, living organisms in soil can exist in cyst-like states during extended periods of seasonal dormancy, and so become resistant to many types of biocidal treatments.

Traditional thinking also indicated that the sometimes high concentration of naturally occurring organic compounds in soil close to the surface of a field can consume large amounts of ozone and so result in insufficient exposure of living organisms in the soil to ozone.

SUMMARY

This invention relates to a method and apparatus for agricultural use of ozone ($O_3$) to sanitize, i.e., kill or weaken living organisms in top soil suitable for plant growth purposes. Ozone has a negligible deleterious effect on the environment because ozone breaks down into simple diatomic oxygen on reaction with an organic or inorganic agent or due to ozone's inherent instability.

In an ozone treatment method and apparatus in accordance with this invention, top soil suitable for plant growth purposes is rendered relatively uniformly homogeneous in texture and allowed to dry and then an ozone containing gas from an ozone supplier is injected through a soil injector into the top soil. In one embodiment, the ozone containing gas is generated by an ozone supplier that can be moved over the field by a structure, such as a trailer or a vehicle. The ozone supplier includes an ozone containing chamber in one embodiment and a corona ozone generator in another embodiment. The ozone containing gas can be injected into the soil immediately subsequent to ozone generation or after pretreatment of the ozone containing gas to stabilize the ozone.

In one embodiment, the ozone treatment method and apparatus can be used in conjunction with traditional agricultural operations such as tilling, fertilization, irrigation, sowing seeds or transplanting plants, spraying herbicides or pesticides, and harvesting crops. As ozone treatment has no known detrimental side-effects in agricultural use on crops for human or animal consumption or use, such ozone treatment can be applied repeatedly as often as necessary. Ozone treatment can be performed once per season or even several times per season, depending on the rate of occurrence of living organisms that are detrimental to plants being grown in the ozone treated soil. Therefore ozone treatment of soil suitable for plant growth purposes in accordance with this invention is functionally effective, environmentally benign, easy to use, and is a suitable replacement for methyl bromide and other fumigating biocides.

In another embodiment, the ozone containing gas is injected into top soil suitable for plant growth purposes using a lattice arrangement of conduits buried in a field. Such an arrangement of conduits allows easy, timely, and frequent application of ozone and can be especially suited for multiple ozone treatments of soil during a growing season when field access is otherwise limited.

In yet another embodiment, the soil is transferred to a chamber and subjected to in-vitro ozone treatment. The soil is exposed to gaseous ozone of sufficient concentration for a sufficient period of time such that the ozone kills a predetermined number, for example a majority, of living organisms in the soil as required for successful subsequent plant growth purposes. Such an in-vitro ozone treatment is especially suited for nursery plants where isolation of soils is often required for certification purposes.

BRIEF DESCRIPTION OF THE DRAWING

FIGS. 4A and 4B illustrate other embodiments of this invention for injecting an ozone containing gas into the soil.

FIG. 4A-1 illustrates an enlarged portion of the embodiment of FIG. 4A.

DETAILED DESCRIPTION

Figure 1:
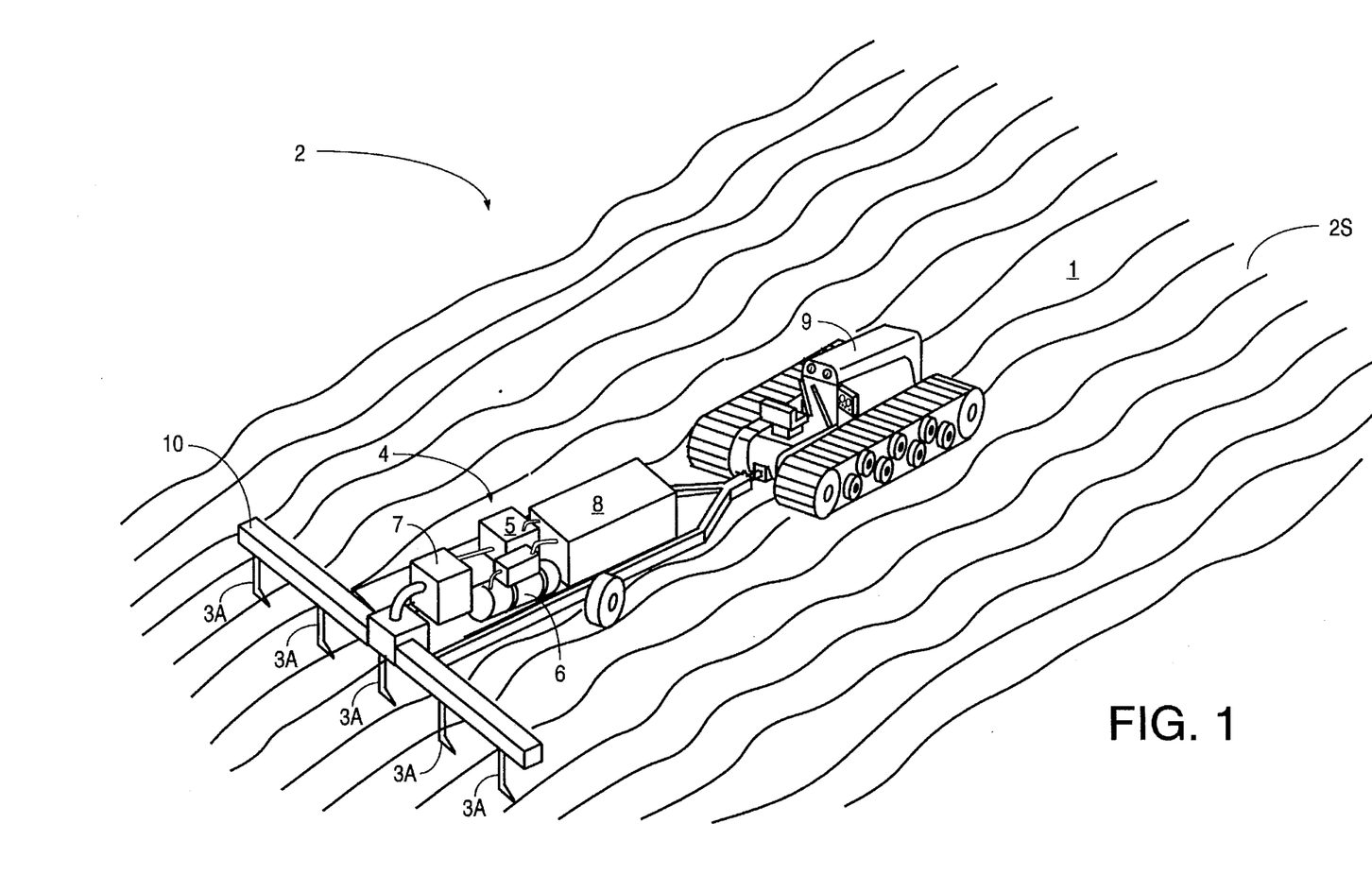
FIGS. 1 and 2 illustrate an embodiment of a method and apparatus for ozone treatment of (1) soil in a field, and (2) soil in a localized environment such as soil for tree vine replants.

FIG. 1 illustrates an embodiment of a method and apparatus for ozone treatment of soil 1 in a field 2. Field 2 is any space used for plant growth purposes including, but not limited to, open or cultivated fields, seed beds, orchards, or vineyards.

Soil 1 is any natural or artificial substance suitable for rooting and plant growth purposes, such as agricultural top soil including clay, sand, rock or organic substrates. Top soil is that soil close enough to the surface to be worked (i.e. plowed, tilted, disced or otherwise operated) by a farmer. Top soil can be soil within depth d (FIG. 3A) from the surface 2S of field 2. For example, "d" can be six feet or four feet or any other appropriate depth. Surface 2S of field 2 conforms to the naturally surface of planet earth and excludes artificial and/or underground surfaces, such as surfaces of injection wells described in U.S. Pat. No. 5,269,943 to Wickramanayake at col. 9, line 47. Therefore, top soil does not include for example, soil adjacent to discharges of injection wells.

Soil 1 is suitable for plant growth purposes and includes a normal amount of organic impurities such as pesticides and herbicides and also includes living biological organisms. In one embodiment, soil 1 is top soil in a field that was recently cultivated for growth of plants, for example strawberries. Typically soil 1 might include some undesirable living organisms, such as verticillium albo/atrum (fungus)—leafwilt, fusarium oxysporum (fungus)—leafwilt, meloidogne spp. (root knot nematode)—root attack/viral transmission, pratylenchus spp. (nematode)—root attack/viral transmission and xiphinema spp. (dagger nematode)— root attack/viral transmission that are preferably killed prior to the next use of soil 1 for growing strawberries.

Soil in a field unsuitable for plant growth purposes includes, for example, soil contaminated with organic compounds, such as those described in U.S. Pat. No. 5,269,943 to Wickramanayake that is incorporated herein in its entirety. An example of soil unfit for plant growth purposes is soil contaminated by accidents, such as spills and leaks from underground storage tanks and, pipelines and tank car derailments, as noted by Wickramanayake. Soil can also be contaminated by, for example, excessive application of pesticides or herbicides and by land disposal of hazardous organic wastes, as noted by Wickramanayake.

Soil 1 is optionally rendered uniformly homogeneous in texture and free of clumps that inhibit free passage of a gas through the soil. A clump is an agglomeration of soil particles that can be physically handled as a group. Physical handling includes, for example, manually lifting a handful of soil 1 from field 2.

Rendering soil 1 homogeneous also exposes the pores in soil particles and the interstitial spaces in clumps that otherwise protect and/or harbor living organisms. Such rendering homogeneous causes a significant portion of a living organism to be exposed to ozone when an ozone containing gas is subsequently applied to homogeneous soil 1, as described below. An ozone containing gas includes, for example, ozone carried in air or ozone carried in oxygen. A significant portion of a living organism is any portion that when destroyed results in death of the living organism, before natural death. An example of a significant portion is an exposed cell. The application of ozone containing gas to homogeneous soil 1 results in subsequent enhanced plant growth, for example as in step 806 (FIG. 8), because ozone kills or weakens undesirable living organisms.

Conventional processes such as shanking, discing, tilling and springtoothing can be used to render soil 1 in field 2 uniformly homogeneous. After such rendering homogeneous, the majority of clumps in the soil have a side less than or equal to, for example 1 inch, 0.50 inch, or 0.25 inch, depending on the extent of processing of soil.

Prior to ozone treatment, soil 1 is allowed to dry or dried by various processes. Drying of soil 1 can avoid the difficulty inherent in moving a gas through compact wet soil, which can result from irrigation water filling interstitial spaces in soil 1. After soil 1 is allowed to dry or dried, for example, with heat or compressed dried air, soil is ozonated by applying an ozone containing gas using a soil injector support device 10 to which soil injectors 3A are attached. Although FIG. 1 shows a number of soil injectors 3A for injecting the ozone containing gas into soil 1, any mechanism conventionally used in application of gases or liquids to soil can be used.

Figure 3A:
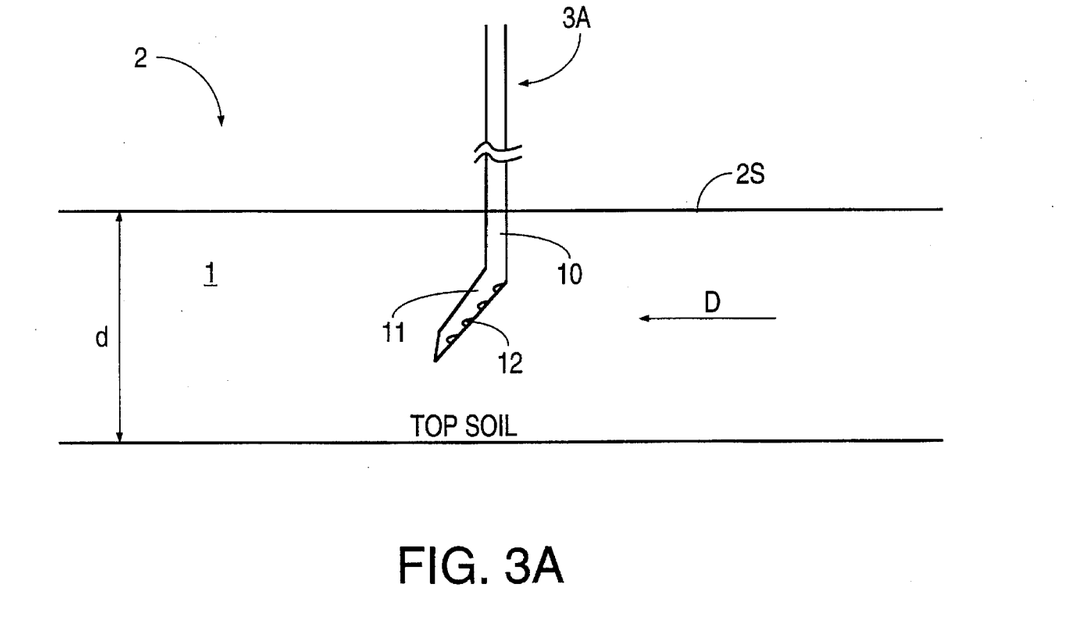
FIGS. 3A and 3B illustrate two embodiments of a soil injector for ozone treatment of soils.

In the embodiment of FIG. 1, soil injectors 3A are placed within a distance not exceeding three feet from the point in the soil at which sanitization is desired. In the embodiment of FIG. 1, soil injectors 3A are three feet apart from each other and extend no more than three feet deep into soil 1 from surface 2S of field 2 (FIG. 3A).

After injection, the ozone containing gas disperses through the interstitial spaces between the soil particles and into pores within the soil particles. Impurities in soil 1 including organic materials are oxidized by ozone. Ozone breaks down large complex organic molecules into smaller molecules and eventually into $H_2O$ and $CO_2$.

In addition to oxidizing organic impurities in soil 1, ozone also kills or weakens living cells and organisms in soil 1 by oxidizing the cell walls. As soil 1 has been rendered substantially uniform, ozone is able to reach and attack the living organisms in soil 1. Moreover, as gaseous ozone has a longer half life than aqueous phase ozone, living organisms in cyst-like state are exposed to a higher concentration of ozone in the gaseous phase for a longer period of time than possible by using aqueous ozone. If the cells in soil 1 are exposed to ozone for a sufficient period of time, lysing of cell walls occurs, releasing the cytoplasm of the cells and causing death of the cells and/or death of a living organism that includes the cells. If the cells are exposed to ozone for less than a period of time sufficient to kill the cells, the living organism is weakened by partial oxidation of cell membranes. Such a weakened living organism is susceptible to other natural or artificial biocidal agents, such as solarization, and eventually dies before natural death. Even if such a weakened living organism is not killed by ozone treatment, such a weakened living organism has a reduced detrimental effect on plants, compared to an untreated living organism.

As soil 1 is free of excessive contaminants, sufficient amount of ozone is available to kill a majority of living organisms, even though some ozone reacts with organic impurities. Moreover, only a small amount of the organic material in the cells of a living organism needs to be oxidized to kill the living organism, and almost all of the organic material from the living organism can remain unoxidized and yet not have any detrimental effect on plant growth. The amount of ozone necessary to kill living organisms is less than the amount of ozone needed for decontamination because in decontamination the majority of the hydrocarbon must be destroyed.

In one embodiment, the following process parameters are associated with the use of ozone to kill biological life forms in soil 1. Soil 1 (a) is fit for plant growth purposes and contains a number of living organisms that are desirably weakened and preferably killed prior to growing plants in soil 1; (b) has a total moisture content at the moment of ozone treatment less than or approximately equal to 20 percent by weight; (c) is at a temperature less than or approximately equal to 110 degrees Fahrenheit. An ozone containing gas (d) has a pressure greater than or approximately equal to 5.0 p.s.i. gauge pressure; (e) has an ozone concentration greater than or approximately equal to 0.1 percent by weight of the gas; (f) is injected into soil 1 at a depth greater than or approximately equal to 6 inches but no greater than or approximately equal to three feet from surface 2S of field 2; (g) is at a temperature less than or approximately equal to 110 degrees Fahrenheit; and (h) after ozone treatment, a time weighted average ozone level in the air over field 2 results in exposure to individuals of less than (1) 0.1 part per million over an eight hour period; and (2) 0.3 part per million over a fifteen minute period.

The depth at which the ozone containing gas is injected is critical to ensure the killing of the majority of living organisms in soil 1. If the ozone containing gas is merely applied to surface 2S of field 2, without being injected into soil 1, only living organisms on surface 2S may be weakened or killed, if the living organisms do not migrate deeper into soil 1 and if the ozone containing gas is not lost into the atmosphere. On the other hand, if the ozone containing gas is injected into an injection well, such as the injection wells described in U.S. Pat. No. 5,269,943 to Wickramanayake at col. 9, line 47, the majority of the living organisms in the top soil of field 2 will remain alive.

The use of ozone in a concentration in the ranges described herein results in acceptable ozone levels over field 2, unlike Wickramanayake's ozone concentrations which result in ozone levels several orders of magnitude larger than the human exposure threshold time weighted average limit of 0.1 part per million (ppm) permitted by the U.S. Occupational Safety and Health Administration Department.

The ozone concentration ranges described herein are also less expensive because there is no need for a quenching compound of the type suggested by Wickramanayake, to limit the levels of ozone in the atmosphere over field 2. Another advantage of this invention is that the use of untreated ozone does not have side effects, such as making the soil too acidic or creating harmful byproducts, for example sulfates and chlorates as described by Wickramanayake (above). So use of untreated ozone can be repeated as often as desired without any undesirable side effects, such as buildup of externally introduced chemicals in the soil.

Ozone containing gas is injected at various points in field 2 such that each injection point is at a distance less than or approximately equal to 3 feet from the farthest point at which sanitization is desired. For effective sanitization of the soil, soil 1 is exposed to the ozone containing gas for a period of time such that the result of multiplication of the ozone concentration and the time period is approximately equal to sixty parts per million-minutes.

Figure 2:
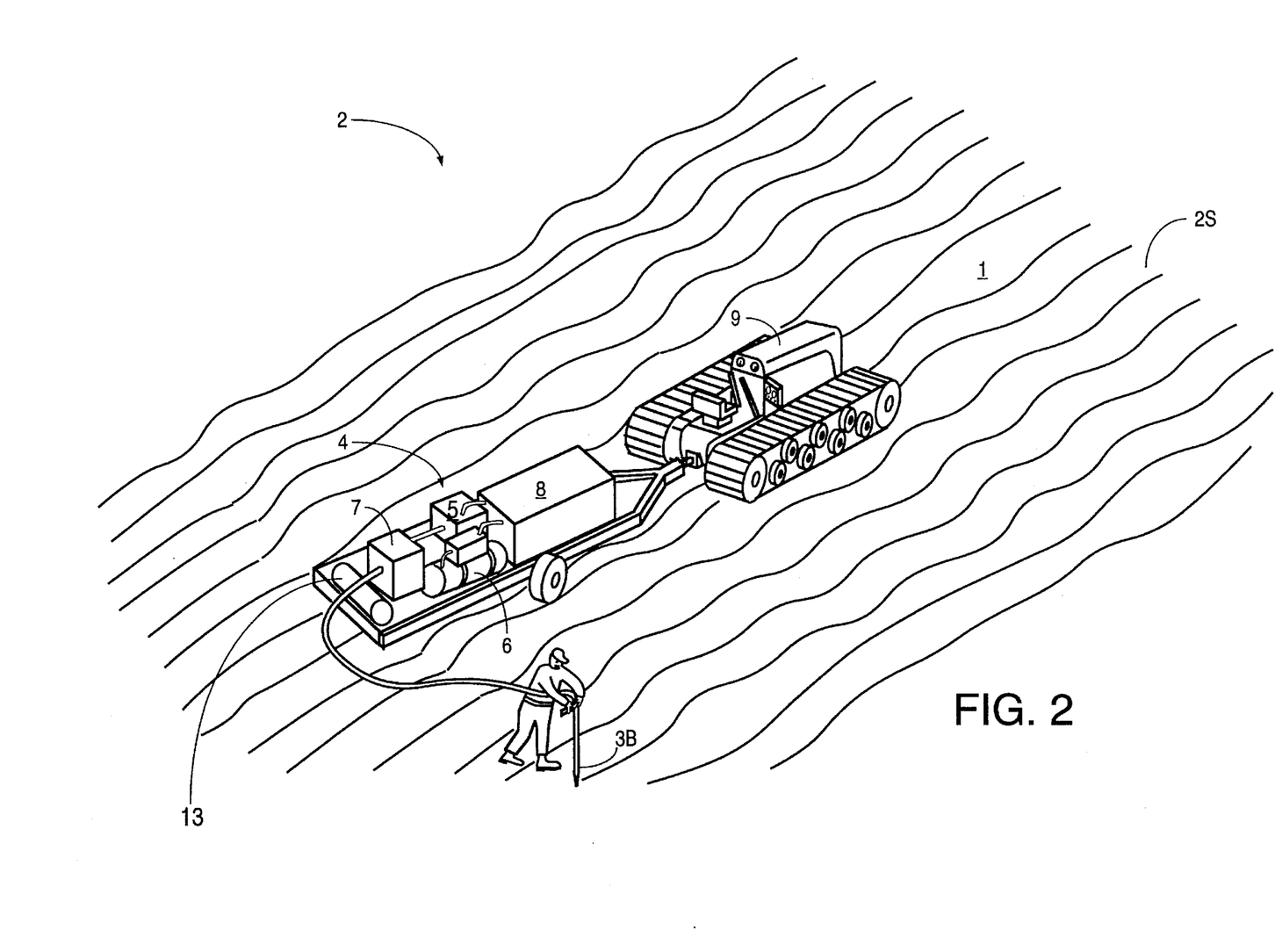

The ozone containing gas is supplied to soil injector 3A or 3B from an ozone supplier 4. Ozone supplier 4 is any device used for supplying an ozone containing gas. For example, ozone supplier 4 can be a Hankin Ozotec model II available from Hankin Atlas Ozone Systems in Scarborough, Ontario Canada. In one embodiment, ozone supplier 4 includes an electric generator 8, an ozone generator with power supply 7, an air compressor 6 and an air purification system 5 (FIGS. 1 and 2).

An ozone supplier can also include an ozone chamber 13 of a size, such as 10 cubic feet, to equalize pressure imbalances or mix or dilute the ozone containing gas with other gaseous elements. (See FIG. 2.) In one embodiment, the ozone containing gas is injected into soil 1 immediately subsequent to ozone generation, without any additional chemical pre-treatment of the ozone containing gas. In another embodiment, prior to injection, the ozone containing gas is stabilized by pretreatment with acid as described by U.S. Pat. No. 5,269,943 to Wickramanayake.

As shown in FIG. 1, ozone supplier 4 is moved by a self propelled field device 9, such as a tractor. Self propelled field device 9 can be replaced by any appropriate vehicle or equipment used for moving ozone supplier 4 relative to soil 1. The ozone supplier 4 is skid or trailer mounted and soil injector 3A is shanked into the ground. In one embodiment, ozone containing gas is generated as well as injected into soil 1 during the movement of self propelled field device 9 over surface 2S of field 2. Such ozone generation during movement has the advantage of low initial capital cost.

An ozone supplier can be incorporated into a vehicle rather than being skid or trailer mounted. Moreover, although FIG. 1 shows ozone containing gas being applied to soil 1 in an open field 2, ozone containing gas can be used in any application in which sanitization is desired. In FIG. 2, a worker is injecting ozone locally into the soil using a hand held injector 3B of the type shown in FIG. 3B. This apparatus is useful, for example to inject ozone into localized regions of soil to kill living organisms around a replant, for example, to kill giconemella spp (nematode)—bacteria canker in citrus and nut/stone fruit replants, where it is not necessary or economical to treat the entire field. A comparison of the lethal efficacy of the embodiment described in reference to FIG. 2 and FIG. 3B with the lethal efficacy shown by methyl bromide is presented in Table 1.

TABLE 1

| Pounds of Ozone or Methyl Bromide Injected (Tarped/ Untarped) | Percent Change in Nematodes (per 500 g of Soil) at 1 foot from Injection Point | | Percent Change in Nematodes (per 500 g of Soil) at 3 feet from Injection Point |
| --- | --- | --- | --- |
| | Ozone | Methyl Bromide | Ozone |
| Control Tarped | 5 | −4 | 7 |
| Control Untarped | −1 | −8 | −4 |
| 0.07 Tarped | 7 | 5 | 0 |
| 0.07 Untarped | 5 | 9 | −13 |
| 0.22 Tarped | −15 | −45 | 8 |
| 0.22 Untarped | −5 | −35 | −18 |
| 0.7 Tarped | −55 | −85 | −7 |
| 0.7 Untarped | −40 | −86 | −16 |
| 2.2 Tarped | −86 | −98 | −15 |
| 2.2 Untarped | −78 | −92 | −10 |

Ozone Injected at 280 scfh, 1.5%, 2–2.5 feet depth, 70 deg F. and 10 p.s.i. in 10' × 10' centers. Centers are blocks of top soil in a field and schf are square cubic feet per hour.

FIG. 3A shows an embodiment of soil injector 3A that can be used with a moving trailer. As shown in FIG. 3A, soil injector 3A includes an extended hollow pipe 10 with an angular end 11 bent in the direction of movement D and having one or more holes 12. Holes 12, through which passes ozone containing gas, are typically backward facing, opposite to direction D, or downward facing to prevent clogging of holes.

Figure 3B:
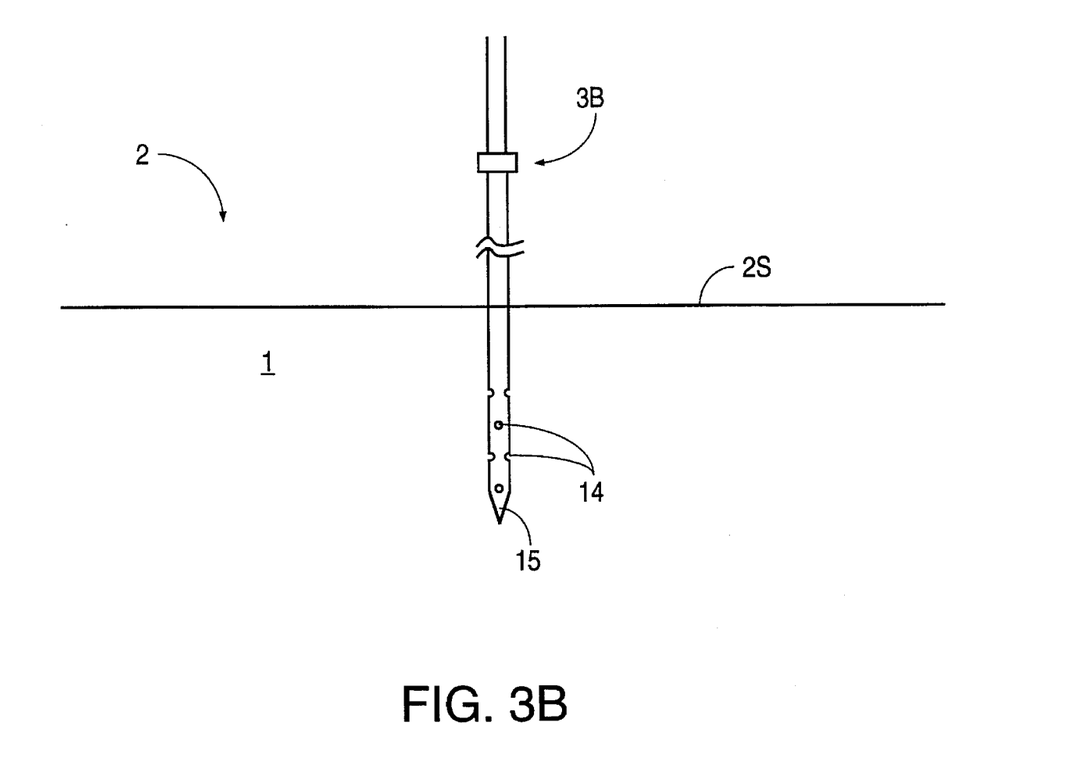

In the embodiment shown in FIG. 3B, soil injector 3B includes an extended, hollow pipe 10, optionally with a sharpened end 15 to facilitate penetration of soil 1 for spot localized soil treatment (FIG. 2). Soil injector 3B has one or more holes 14 through which the ozone containing gas is injected into soil 1.

Although two embodiments of soil injectors are illustrated in FIGS. 3A and 3B, any conventional soil injector can be used. Furthermore, a soil injector can be either stationary or moveable, permanent or temporarily placed in accordance with this invention.

Figures 4A, 4A:
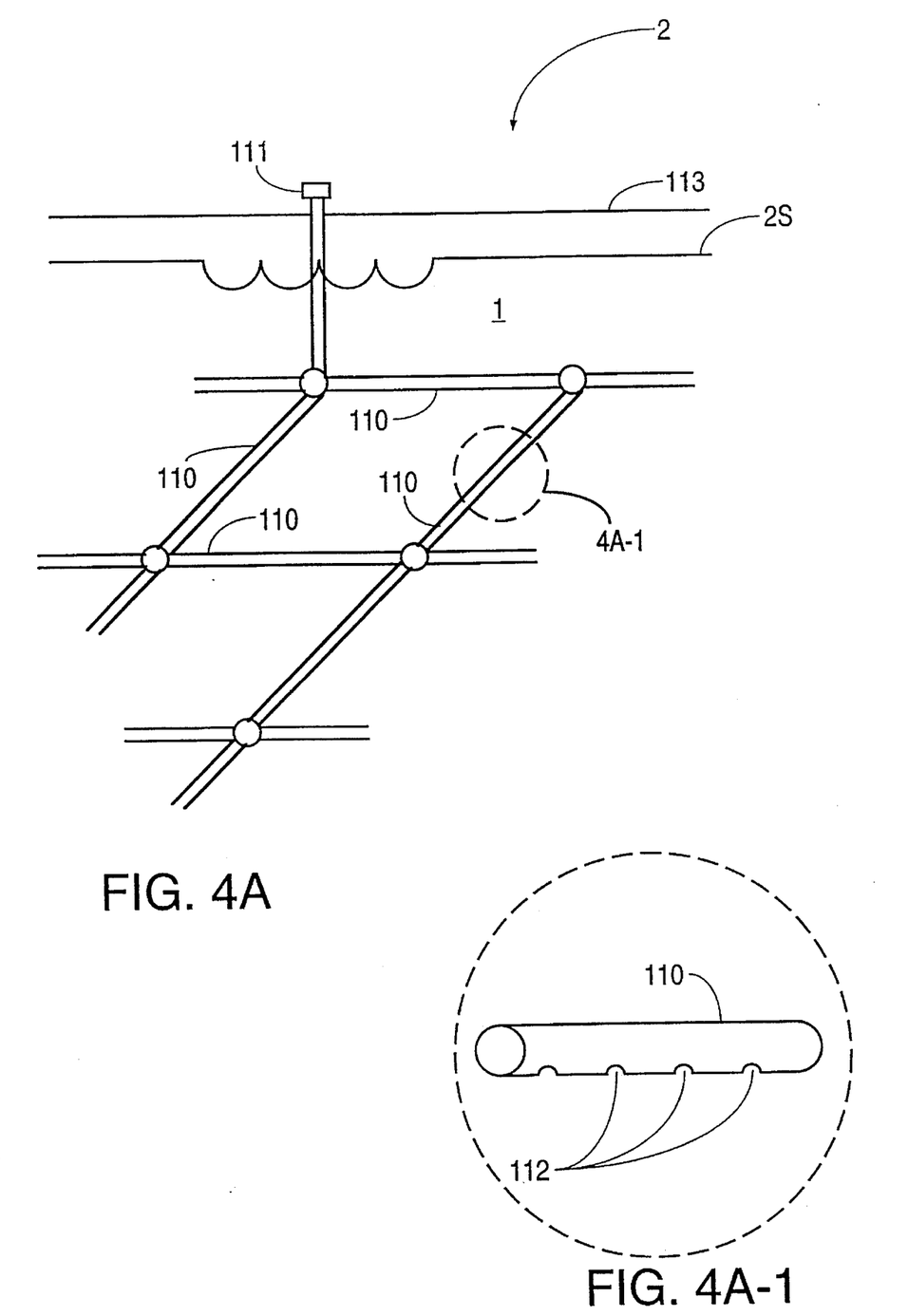

In FIG. 4A, an arrangement of hollow conduits 110 is buried under the surface of field 2. Although a generally rectangular lattice configuration of conduits 110 is illustrated in FIG. 4A, conduits 110 can be arranged in any manner appropriate for injecting a gas into the soil in accordance with this invention.

In FIG. 4A, the ozone containing gas enters at conduit inlet 111 of the conduit lattice, is transmitted through conduits 110 and is injected into soil 1 through holes 112 in conduits 110 (see inset enlargement of conduit 110 in FIG. 4A-1).

In one embodiment, conduits 110 are polyvinyl chloride (PVC) pipes. Any ozone resistant piping held together by ozone resistant fittings, welds, or glue can also be used, instead of PVC pipes and includes, for example stainless steel or teflon.

Conduits 110 can be used for other purposes such as underground irrigation or fertilization when conduits 110 are not used for injecting ozone containing gas into soil 1.

Figure 4B:
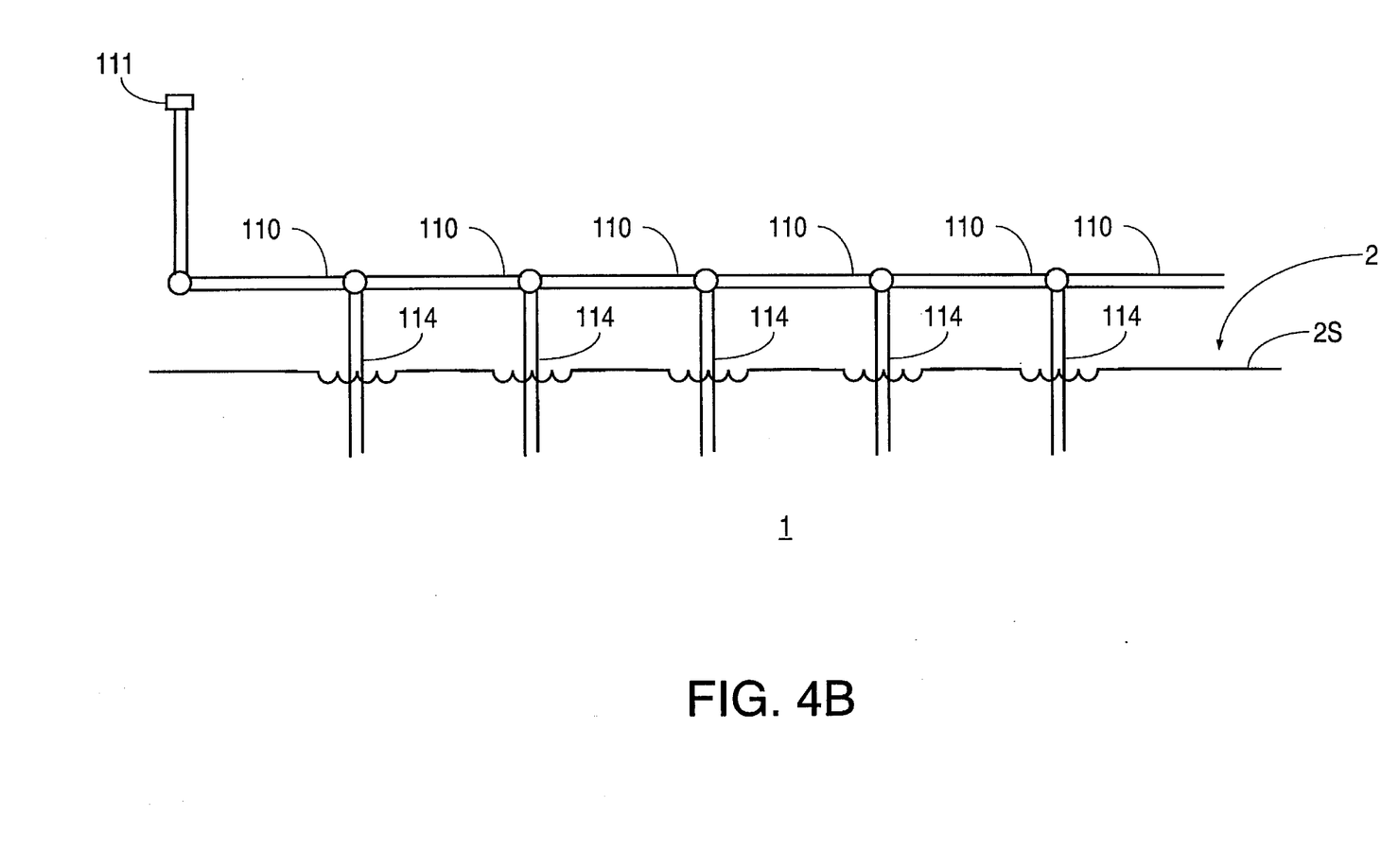

FIG. 4B shows an arrangement of hollow conduits 110 disposed horizontally on or over a surface 2S of field 2. The arrangement in FIG. 4B includes a conduit inlet 111 and vertical conduits 114 with open ends inserted into soil 1. A conduit 114 can be a simple hollow conduit with an open end for discharging the ozone containing gas. Alternatively, a conduit 114 can be any conventional soil injector or one of soil injectors 3A or 3B described above in reference to FIG. 3A or 3B.

Soil 1 is optionally covered with a gas impermeable or semi-impermeable membrane 113 (FIG. 4A) immediately subsequent or prior to injection of the ozone containing gas (tarping). Tarping serves to keep the ozone containing gas within soil 1 thus: (1) minimizing untoward detrimental emissions of ozone into the atmosphere, (2) minimizing ozone production costs and (3) resulting in a synergistic solarization effect.

As used herein, the term "solarization" means the effect of tarping, or covering the soil to decrease heat losses from the soil to the atmosphere and to increase the ambient temperature of the soil due to the green-house effect. When combined with ozone treatment, tarping further reduces detrimental biological activity in soil 1. Although membrane 113 is shown only in FIG. 4A, membrane 113 can also be advantageously used in other embodiments such as FIGS. 1 and 2. The tarping equipment may be manual or automatic and may be incorporated into the soil injector support device 10 carrying soil injectors 3A (FIG. 1). Preferably, tarping is immediately subsequent to the injection of ozone.

A demonstration of the lethal efficacy of ozone containing gas pumped by the lattice arrangement described above in reference to FIG. 4A is presented in Table 2.

TABLE 2

| Pounds of Ozone Injected per 4 sq. ft. | Percent Change in Total Bacteria (per gram of Soil) |
| --- | --- |
| Control Tarped | −4 |
| Control Untarped | 6 |
| 0.1 Tarped | −11 |
| 0.1 Untarped | −2 |
| 0.5 Tarped | −15 |
| 0.5 Untarped | −12 |
| 2.5 Tarped | −82 |
| 2.5 Untarped | −68 |

Ozone Injected at 280 scfh 1.5% concentration at 2.5 feet depth in 2 feet × 2 feet grid (i.e., 10 cf of soil).

Ozone can be made from air or from oxygen. Air yields a typical concentration of ozone by weight of up to 2%. Highly concentrated oxygen (90% to 98%) typically yields a concentration of ozone by weight up to 4% to 6%. The carrier gas in an ozone containing gas can be air, oxygen or other gas that contains oxygen.

Figure 5:
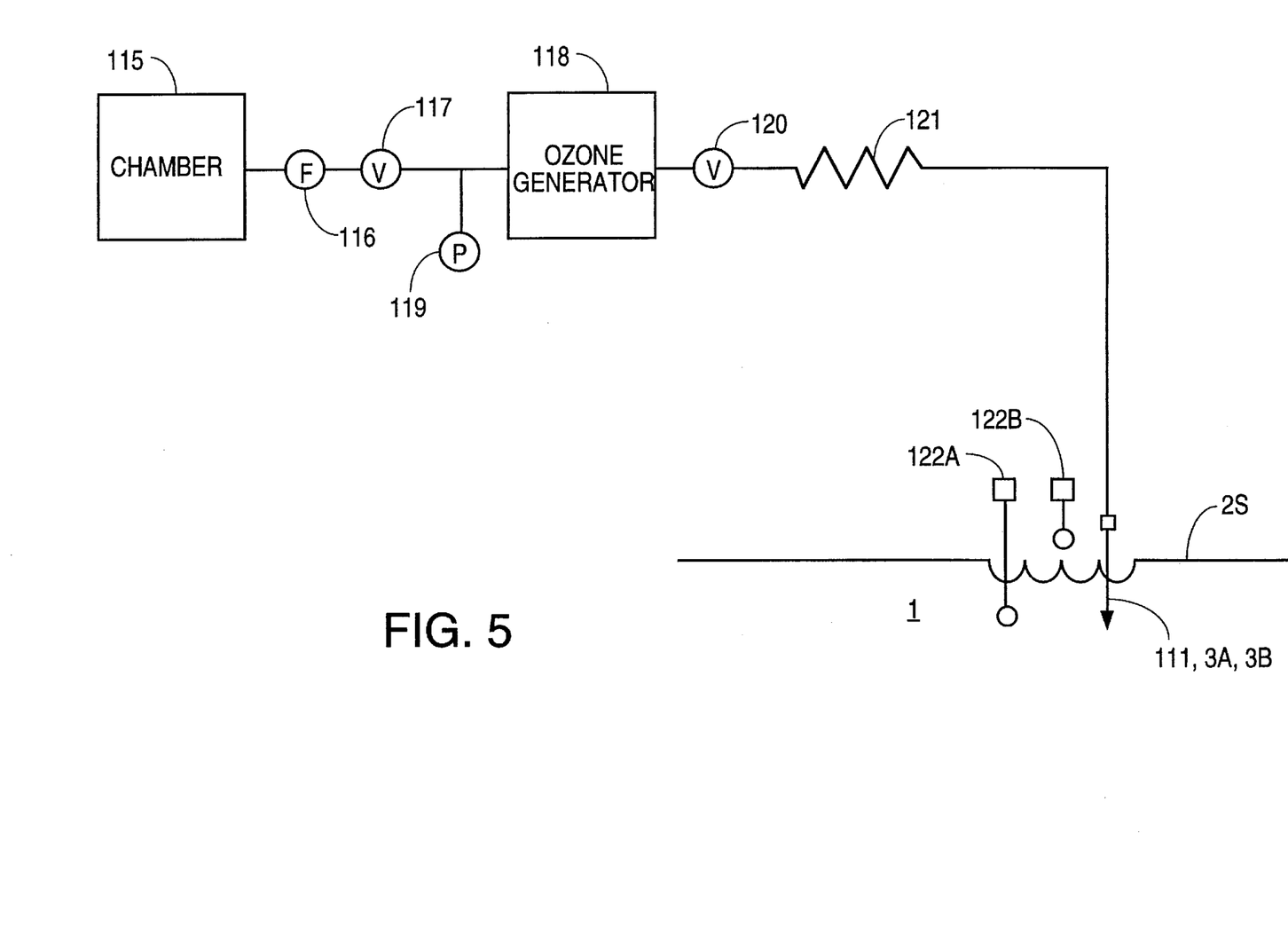
FIGS. 5 and 6 are block diagrams illustrating in-situ and in-vitro ozone treatment of soil respectively.

Using the equipment schematically illustrated in FIG. 5, dried oxygen containing gas (a gas that contains oxygen from which moisture has been substantially removed) is produced in chamber 115 by a conventional process such as an air compressor followed by refrigeration, pressure swing absorption with silica desiccant, molecular sieve, or membrane separation. The dried oxygen containing gas is supplied via a conduit to a filter 116 prior to generation of ozone. Filter 116 can be a particulate or hydrocarbon filter.

One or more valves 117 control(s) the pressure of the dried purified oxygen containing gas supplied to ozone generator 118, to optimize ozone output and limit over pressurization. Over pressurization can damage components such as electrodes of ozone generator 118 and can occur, for example, when the oxygen containing gas entering ozone generator 118 exceeds 25 p.s.i.g. Valve 117 is a standard, off-the-shelf pressure regulating valve.

Ozone generator 118 can be a conventional corona ozone generator or one of a number of different well known variants thereof. A standard pressure indicator device 119 is generally provided to monitor the pressure at which oxygen and other gases are introduced into the ozone generator and subsequently into soil injector 3A or 3B or lattice conduit inlet 111. Valve 120, such as a standard 316 stainless steel valve, controls the amount of ozone provided via conduit 121 to injector 3 or inlet 111. (See FIGS. 1, 2, 3A, 3B, 4A and 4B.) Conduit 121 can be a rigid conduit, such as standard 1" 316 stainless steel piping or a flexible conduit, such as standard 1" schedule 40 PVC pipe.

An ozone gas concentration measuring device 122A is optionally provided in soil 1 at a distant point from the point of injection of the ozone containing gas to determine the actual concentration of ozone in soil 1. In the embodiments described in reference to FIGS. 2, 4A, and 4B, ozone gas concentration measuring device 122A is optionally placed between 6 inches and 3 feet from a point of ozone injection into the soil. Ozone gas concentration measuring device 122B is optionally provided to determine the amount of ozone emitted from soil 1 into the atmosphere. Concentration measurements from measuring device 122A or 122B can be used to estimate the end point of the ozone injection process for achieving the desired results. Ozone gas concentration measuring devices 122A and 122B can be any conventional devices such as an Ozometer available from Hankin Atlas Ozone Industries of Scarborough, Ontario, Canada.

In addition to the in-situ ozone treatment of soil described above, soil 1 can be treated in-vitro. In-vitro ozone treatment of soil 1 may be necessary (1) in greenhouse applications, (2) in applications requiring greatly reduced ozone emissions for environmental reasons or (3) for reducing damaging effects on other biological organisms in the field.

Figure 6:
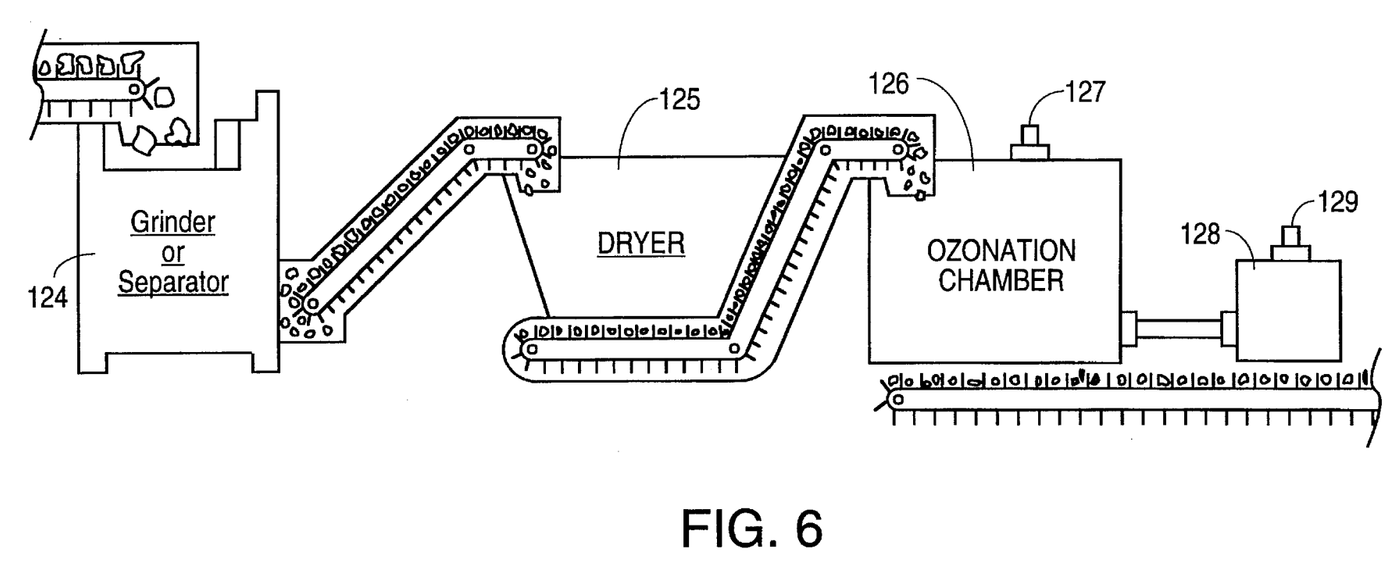
Figure 7:
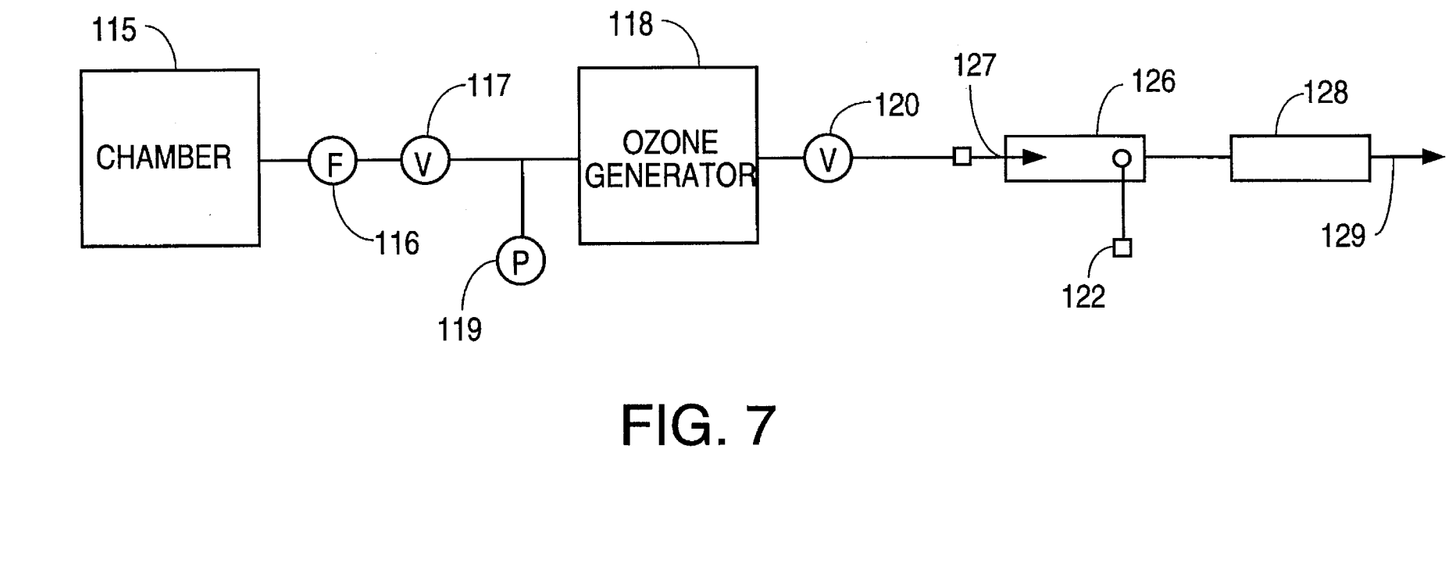
FIG. 7 is a block diagram illustrating the in-vitro ozone treatment apparatus and method shown in FIG 6.

In the embodiment shown in FIGS. 6 and 7, top soil 1 (FIG. 1) suitable for plant growth purposes is removed from a field 2 for in-vitro treatment. Soil 1 having clods and agglomerated clumps is placed in an apparatus 124 (FIGS. 6 and 7). Apparatus 124 can be a grinder or a separator that renders soil 1 from field 2 (FIG. 1) relatively uniformly homogenous by conventional process such as grinding and mixing or screening and/or similar processing of soil 1.

The relatively uniform soil 1 is then transferred to a dryer 125 and dried or allowed to dry until the total moisture content is less than or approximately equal to 20 percent. The dried soil 1 is exposed to an ozone containing gas in ozonation chamber 126 at an ozone containing gas temperature or soil temperature less than or approximately equal to 110 degrees fahrenheit. The optimal maximum upper temperature is 110 degrees fahrenheit because ozone very rapidly reverts back into diatomic oxygen at temperatures approximately exceeding 110° F. Optimal ozone lifetimes are achieved when the temperature is minimized to the greatest extent possible. The temperature of soil 1 can even be below the freezing point of water.

The ozone containing gas is supplied at inlet 127 of ozonation chamber 126 from an ozone generator 118 (FIG. 7). In FIGS. 6 and 7, ozonation chamber 126 is an enclosure which holds soil 1 and into which ozone containing gas is injected. Ozonation chamber 126 of FIGS. 6 and 7 can be any size pipe or chamber with ozone going in at one end and out at the other end.

The gases vented from ozonation chamber 126 are directed through a conduit to a deozonation chamber 128. Deozonation chamber 128 contains a catalyst to destroy any unconsumed ozone. The catalyst in deozonation chamber 128 can be activated carbon, manganese dioxide, or any other catalyst capable of destroying ozone or causing reversion of ozone to oxygen. Optionally, the vented gases may be heated to thermally destruct any ozone. The deozonated gases at outlet 129 of deozonator chamber 128 are environmentally safe and can be vented to the outside world.

A demonstration of the lethal efficacy of the reductions in biological activity due to in-vitro treatment of soil 1 in the manner described above in reference to FIGS. 6 and 7 is presented in Table 3.

TABLE 3

| Ozone Gas Concentration (ppm) | Exposure Time (minutes) | Concentration × Time (ppm - min) | Percent Change in Total Baceria (per gram of Soil) |
|---|---|---|---|
| Control | 60 | | −5 |
| Control | 240 | | 8 |
| 0.05 | 60 | 3 | −11 |
| 0.05 | 240 | 12 | −17 |
| 0.25 | 60 | 15 | 5 |
| 0.25 | 240 | 60 | −62 |
| 1 | 60 | 60 | −81 |
| 1 | 240 | 240 | −88 |
| 4 | 15 | 60 | −79 |
| 4 | 60 | 240 | −83 |
| 16 | 15 | 240 | −91 |
| 16 | 60 | 960 | −92 |

Ozone Injected at 70 deg F. and 10 p.s.i. into cylinder of soil 18" long × 2" diameter at an injection rate of 100 scfh.

As seen from Tables 1, 2 and 3, injection of sufficiently concentrated ozone containing gas at a relatively low pressure and temperature into relatively homogenous and dry soil 1 and exposure of the soil-borne living organisms to the ozone for a minimum period of time (dependent on the ozone concentration) reduces biological activity in soil 1.

In one specific embodiment, when soil 1 is exposed to ozone containing gas such that the result of multiplication of a concentration of the ozone in the gas and the period of time of exposure is greater than or approximately equal to sixty parts per million-minutes, a majority of the living organisms are killed. For example in Table 3, ozone gas concentration of 0.25 ppm and exposure time of 240 minutes results in killing a majority (greater than 50%, and in this case 62%) of total bacteria.

Furthermore, tarping maximizes sanitization of soil 1 while simultaneously minimizing emissions of ozone gas into the atmosphere, minimizing the use of ozone and therefore reducing the expenditure of power otherwise necessary to produce the ozone gas.

The levels of ozone in the air in the experiments reported in Tables 1, 2 and 3 were measured and found to be below the detection threshold of the instruments of 0.1 ppm, and thus are safe for in-situ application of ozone without exceeding levels allowed by the U.S. Occupational Safety and Health Administration Department. The slight positive increase in living organisms shown in some treatments in Tables 1, 2, and 3 can be due to the variability of the populations of living organisms in soils as compared to the untreated control soil samples.

Figure 8:
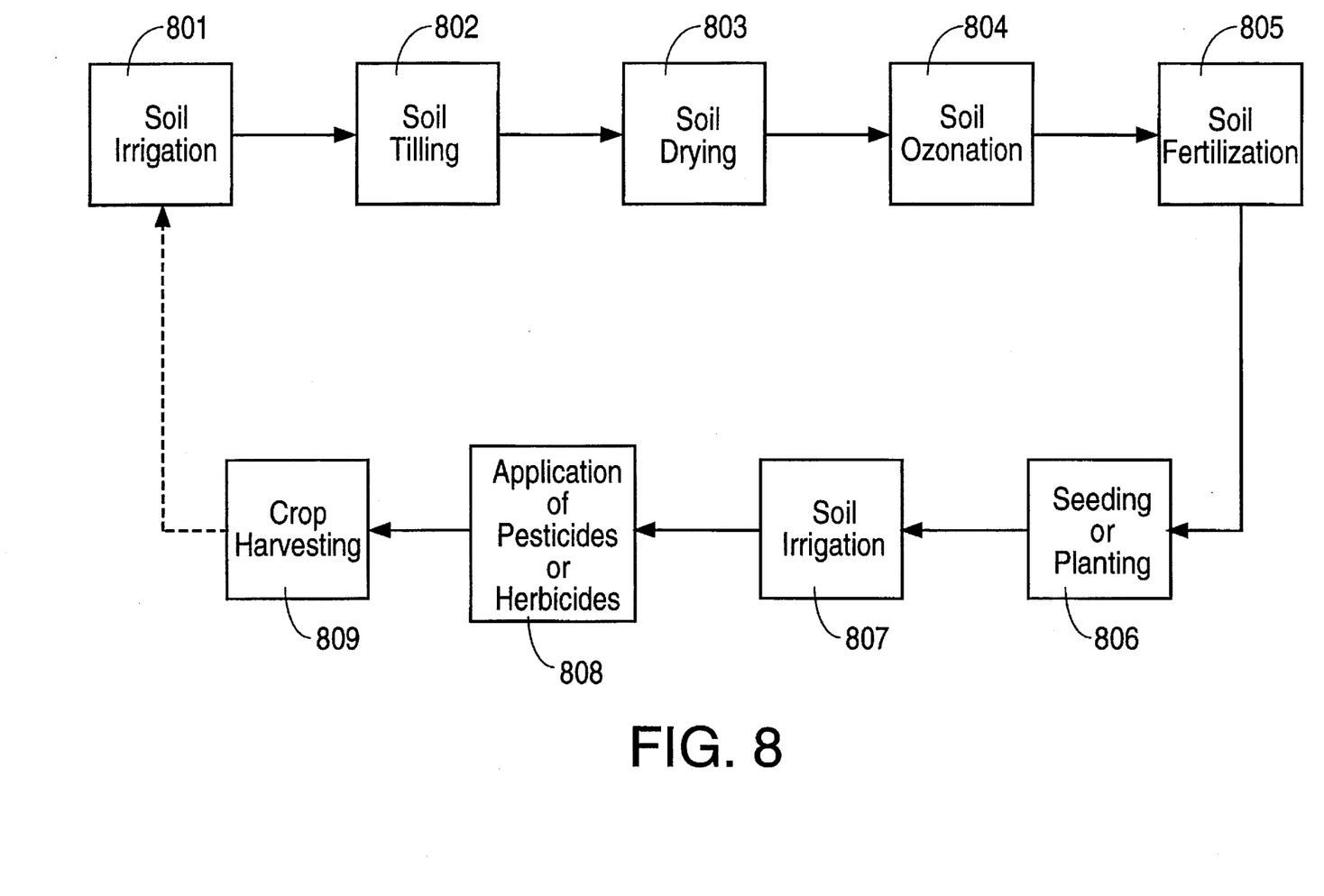
FIG. 8 illustrates a method for using ozone in conjunction with agricultural methods to grow plants in one embodiment.

The method and apparatus for ozone treatment of soil suitable for plant growth purposes can be used in conjunction with other agricultural methods such as irrigation, fertilization and tilling. As illustrated in FIG. 8 in one embodiment, soil 1, fit for plant growth purposes, is irrigated in step 801. Soil 1 can be top soil of a field 2 (FIG. 1) that was previously cultivated. Alternatively, the soil in step 801 can be soil used for other purposes and yet suitable for plant growth purposes. Soil 1 is irrigated in step 801 with sufficient water to ensure proper moisture for the next step of tilling 802, without resulting in soil compaction that can be detrimental to subsequent plant growth.

Instead of or in addition to tilling 802, other methods of rendering soil homogenous, such as shanking, discing, and springtoothing can also be used to ensure that soil 1 has the majority of clumps no larger than 0.25 inch, in this embodiment.

In this embodiment soil 1 is then allowed to dry naturally in step 803 by exposure to sun, until the total moisture content of soil 1 is less than or approximately equal to 20%. In another embodiment, soil 1 is dried artificially by pumping dried or heated air in excess of 120° F. through conduits 110.

Then in step 804, soil 1 is treated with an ozone containing gas, as described above. Then in step 805, soil 1 is fertilized with fertilizers such as calcium nitrate.

Then in step 806, seeds are sown or seedlings transplanted in soil 1. The plants from seeds or seedlings experience enhanced growth due to absence of detrimental biological organisms that were killed in step 804. Then in step 807, soil 1 is once more irrigated. Then in step 808 herbicides or other pesticides may be sprayed or applied over the plants or soil. Then in step 809, the crop is harvested. In the embodiment of FIG. 8, these steps can be repeated for another season by starting at step 801 after completion of step 809. In one embodiment, conduits 110 (FIG. 4A) are used for irrigation in step 801, fertilization in step 805, and pesticide or herbicide application in step 808.

Therefore, treatment of soil with an ozone containing gas is easy and results in significant efficiency in killing the majority of living biological organisms in soil 1 in an environmentally benign manner and provides a much needed alternative to methyl bromide. The killing of living organisms with ozone containing gas that results in low ozone concentrations above surface 2S of field 2, beneath allowable human exposure levels, is an unexpected result that can revolutionize agriculture.

The above description of various embodiments of this invention is intended to be merely illustrative and not limiting. Numerous other embodiments will be apparent to those skilled in the art, all of which are included in the broad scope of this invention. Although in one embodiment, soil 1 is ozonated after irrigation, tilling and drying the soil, soil 1 can be ozonated at any time, for example prior to irrigation or immediately after harvesting. Also, soil 1 can be treated with methyl bromide or other pesticidal agents prior to, during or subsequent to ozonation or some combination thereof. Moreover, by selective ozonation during growth of plants, undesirable weeds can also be destroyed. Although this description refers to killing of a majority of living biological organisms in soil 1, any predetermined percentage of specific living biological organisms, for example, giconemella spp, can be killed by appropriately selecting various parameters, within ranges described herein, to achieve a predetermined success rate in growth of specific plants, such as citrus and nut/stone fruit replants.

What is claimed is:

1. A process for killing living organisms in top soil in a field, said process comprising:
   generating a gas, said gas comprising unacidified ozone and a carrier gas;
   injecting said gas into said top soil, from a naturally occurring surface of said field, said soil being suitable for plant growth purposes prior to said injecting, said soil comprising a plurality of living organisms, said injecting oxidizing at least a majority of said living organisms to weaken said living organisms such that said living organisms eventually die before their natural death.

2. The process of claim 1 wherein said soil of said field is exposed to ozone for a period of time such that the product of said ozone concentration in gas and said time is approximately equal to sixty parts per million-minutes.

3. The process of claim 1 wherein said soil of said field is exposed to unacidified ozone for a period of time such that a result of multiplication of a concentration of said ozone in said gas and said period of time is greater than sixty parts per million-minutes and wherein a time weighted average ozone level in the air over said field results in exposure to individuals of less than
   (a) 0.1 part per million in eight hours; and
   (b) 0.3 part per million in fifteen minutes.

4. The process of claim 1 wherein said ozone concentration approximately equals to 0.1 part per million by weight of said gas.

5. The process of claim 1 wherein said ozone is in a concentration greater than 0.1 part per million by weight of said gas and a time weighted average ozone level in the air over said field results in exposure to individuals of less than
   (a) 0.1 part per million in eight hours; and
   (b) 0.3 part per million in fifteen minutes.

6. The process of claim 1 further comprising a step of rendering said soil relatively homogeneous in texture prior to said injection step.

7. The process of claim 6 wherein said rendering is such that a majority of clumps in said soil after said rendering have a dimension less than or equal to 0.5 inch.

8. The process of claim 1 further comprising a step wherein said soil is allowed to dry prior to said injection step.

9. The process of claim 8 wherein said soil is allowed to dry to less than or equal to 20% moisture by weight.

10. The process of claim 1 further comprising a step of covering said soil with a gas impermeable membrane.

11. The process of claim 1 further comprising a step of covering said soil with a gas semipermeable membrane.

12. A process for sanitizing soil in a field, said soil comprising a plurality of particles separated by a plurality of interstitial spaces, at least one of said particles comprising a living organism, said living organism comprising at least one cell, said cell comprising a cell wall, said process comprising the steps of:
   moving an ozone supplier over said soil of said field;
   generating a gas comprising ozone ($O_3$) during said moving;
   injecting said gas into said soil of said field to approximately fill at least one of said plurality of interstitial spaces; and
   exposing said cell wall to said gas for a period of time sufficient to oxidize a portion of said cell wall.

13. A process comprising:

(a) irrigating soil, said soil being top soil adjacent the naturally occurring surface of a field, said soil being suitable for plant growth purposes prior to said irrigating, said soil comprising a plurality of living organisms;

(b) tilling said soil;

(c) drying said soil;

(d) generating a gas, said gas comprising ozone ($O_3$) and a carrier gas;

(e) injecting said gas into said soil to kill at least one of said living organisms;

(f) sowing or planting in said soil; and (g) reaping a harvest of plants.

14. The process of claim 13 wherein said sequence of steps (a) to (g) are repeated at least once after said step (g).

* * * * *